United States Patent [19]

Reichert et al.

[11] Patent Number: 5,460,956
[45] Date of Patent: Oct. 24, 1995

[54] METHOD FOR PREPARING INTERFERON ALPHA-2 CRYSTALS

[75] Inventors: Paul Reichert, Montville; Gerald S. Hammond, East Orange; Hung V. Le, Rockaway; Tattanahalli L. Nagabhushan, Parsippany; Paul P. Trotta, Secaucus, all of N.J.

[73] Assignee: Schering Corporation, Kenilworth, N.J.

[21] Appl. No.: 952,840

[22] PCT Filed: Jun. 3, 1991

[86] PCT No.: PCT/US91/03660

§ 371 Date: Dec. 1, 1992

§ 102(e) Date: Dec. 1, 1992

[87] PCT Pub. No.: WO91/18927

PCT Pub. Date: Dec. 12, 1991

Related U.S. Application Data

[63] Continuation of Ser. No. 533,225, Jun. 4, 1990, abandoned.

[51] Int. Cl.$^6$ .............. C07K 14/56; C12P 21/00; A61K 38/21
[52] U.S. Cl. ............... 435/69.51; 424/85.7; 530/351
[58] Field of Search ............... 530/351; 424/85.1, 424/85.7; 435/69.51

[56] References Cited

U.S. PATENT DOCUMENTS 2,882,203 4/1959 Petersen et al. ............... 514/3
4,315,852 2/1982 Leibowitz et al. ............ 530/351
4,672,108 6/1987 Kung et al. ................. 530/351

FOREIGN PATENT DOCUMENTS 0281299 9/1988 European Pat. Off..

OTHER PUBLICATIONS

T. L. Nagabhushan, et al. Interferon: Research, Clinical Application & Regulatory Consideration, pp. 79–88. (1982).
David L. Miller, et al. Science 215, pp. 689–690, 5 Feb. 1982.
C. Weissmann, et al., Structure and expression of human IFN–a genes Phil. Trans. R. Soc. Lond. B299, 7–28 (1982).
Alexander McPherson, Preparation and Analysis of Protein Crystals. John Wiley & Sons, pp. 102–104. (1982).
Sydney Pestka, et al., Interferons and Their Actions. Ann. Rev. Biochem. 1987. 56:727–77.
Michael Steuli, et al, At Least Three Human Type a Interferons: Structure of a2., Science 209, 19 Sep. 1980.
Senadhi Vijay–Kumar, et al. Crystallization and Preliminary X–ray Investigation of a Recombinant Form of Human α–Interferon, pp. 4804–4805, (1987).
K. Henco, et al. Structure Relationship of Human Interferon Alpha Genes and Pseudogenes, J. Mol. Bio. (1985) 185, 227–260.
Interferon Y Biotechnologia vol. 5, No. 3 Sep. 1988, Havana–Cuba pp. 281–287, A. Diaz: La Cristalizacion del Interferon Alpha–2 Recombinante Humano.

Primary Examiner—Mindy B. Fleisher
Assistant Examiner—Philip W. Carter
Attorney, Agent, or Firm—Paul G. Lunn; James R. Nelson; Norman C. Dulak

[57] ABSTRACT

A method for making crystals of interferon alpha-2 and the use thereof in depot formulations are disclosed.

8 Claims, No Drawings

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 165 amino acid residues
( B ) TYPE: amino acid
( D ) TOPOLOGY: linear ( i i ) MOLECULE TYPE: peptide ( x i ) SEQUENCE DESCRIPTION: SEQ ID NO: 1:

```
Cys Asp Leu Pro Gln Thr His Ser Leu Gly Ser Arg Arg Thr Leu Met
                  5                  10                 15
Leu Leu Ala Gln Met Arg Arg Ile Ser Leu Phe Ser Cys Leu Lys Asp
            20                  25                  30
Arg His Asp Phe Gly Phe Pro Gln Glu Glu Phe Gly Asn Gln Phe Gln
        35                  40                  45
Lys Ala Glu Thr Ile Pro Val Leu His Glu Met Ile Gln Gln Ile Phe
    50                  55                  60
Asn Leu Phe Ser Thr Lys Asp Ser Ser Ala Ala Trp Asp Glu Thr Leu
65                  70                  75                  80
Leu Asp Lys Phe Tyr Thr Glu Leu Tyr Gln Gln Leu Asn Asp Leu Glu
                85                  90                  95
Ala Cys Val Ile Gln Gly Val Gly Val Thr Glu Thr Pro Leu Met Lys
            100                 105                 110
Glu Asp Ser Ile Leu Ala Val Arg Lys Tyr Phe Gln Arg Ile Thr Leu
        115                 120                 125
Tyr Leu Lys Glu Lys Lys Tyr Ser Pro Cys Ala Trp Glu Val Val Arg
    130                 135                 140
Ala Glu Ile Met Arg Ser Phe Ser Leu Ser Thr Asn Leu Gln Glu Ser
145                 150                 155                 160
Leu Arg Ser Lys Glu
                165
```

METHOD FOR PREPARING INTERFERON ALPHA-2 CRYSTALS

The present application is the United States national application corresponding to International Application No. PCT./US91/03660 filed Jun. 3,1991 and designating the United States, which PCT application is in turn a continuation of U.S. application Ser. No. 07/533,225, filed Jun. 4, 1990, now abandoned the benefit of which applications are claimed pursuant to the provisions of 35 U.S.C. §§120,363, and 365(C).

BACKGROUND OF THE INVENTION

The human interferon alphas are a family of proteins comprising at least 24 subspecies, Zoon K.C., *Interferon* 9, 1–12 (1987), Gresser I., ed. Academic Press, New York. They were originally described as agents capable of inducing an antiviral state in cells but are known as pleiotropic lymphokines affecting many functions of the immune system, Opdenakker, et al., *Experimentia* 45, 513–520 (1989). Apart from their in vitro biological activities the human Interferon alphas are currently used for several important indications, e.g. hairy cell leukemia, Kaposi Sarcoma, veneral warts, and are being investigated for several others *Intron A (interferon alpha-2b) Clinical status* (1989) Proceedings from a satellite symposium at the 5$^{th}$ European Conference on Clinical Oncology, London, U.K. September 1989. The demand for highly purified and crystalline forms of interferon alpha, especially the recombinant type alpha-2b is of foremost importance for structure elucidation as well as for formulation of vadous dosage forms.

Two forms of crystalline human interferon alpha-2 have been reported. Miller et al., *Science,* 215, 689–690 (1982); Kung et al., U.S. Pat. No. 4,672,108; Weissmann, The Cloning of interferon and other Mistakes, In: *Interferon* 1981, Ion Gresser, ed., Academic Press, New York, 101–134; Weissmann, *Phil. Trans. R. Soc. Lond.,* B299, 7–28 (1982); and Nagabhusban, et al., Characterization of Genetically Engineered Alpha-2 Interferon, In: *Interferon: Research Clinical Application and Regulatory Consideration,* Zoon, et al., Elsevier, New York 79–88 (1982). These publications describe methods for crystallizing interferon alpha-2 from polyethylene glycol at low temperature or from a phosphate buffer solution by adjusting the pH or temperature. These methods normally provide needle crystals which cannot be well characterized by X-ray diffraction techniques. The Miller et al. article also mentions crystalline interferon alpha-2 in a "prismatic form".

In general, the methods for crystallizing proteins such as interferon have been found to be unpredictable. For example, Kung et al., U.S. Pat. No. 4,672,108 (1987) specifically states in column 1, lines 52–64:

"Numerous techniques have been developed for the crystallization of proteins, however, no generalized procedure has been discovered, and many proteins remain uncrystallized. Thus, crystallization of proteins is an unpredictable art utilizing tdal and error procedures among many possible alternative methodologies.

One of the most widely used approaches involves the addition to the protein solution of a crystallizing agent, which is commonly a salt, such as ammonium sulfate or ammonium citrate or an organic solvent, such as ethanol or 2-ethyl-2,4-pentanediol. However, such procedures do not provide a suitable means for producing crystalline human leukocyte interferons." (Emphasis added.)

SUMMARY OF THE INVENTION

We have now surprisingly found that high quality crystalline interferon alpha-2 can be produced efficiently even at room temperature by a method which comprises equilibrating a solution of interferon alpha-2 against a sulfate salt solution that will cause the interferon alpha-2 solution to become more concentrated and form interferon alpha-2 crystals. Preferably, the equilibration is effected by means of ultrafiltration or dialysis, or using drops, e.g., by hanging or sandwiched droplets.

The solution of interferon alpha-2 preferably contains a sulfate salt, and this solution is preferably equilibrated against a more concentrated sulfate salt solution. The sulfate salt is preferably selected from an ammonium, calcium, cadmium, potassium, lithium, magnesium or sodium salt, more preferably it is ammonium sulfate. The sulfate salt is preferably present in the crystalline interferon alpha-2 solution at the time crystals begin to form in a concentration of from about 12% to about 30% saturated, more preferably in a concentration of from about 15% to about 25% saturated ammonium sulfate. As noted below, the concentration of sulfate salt at the start of the equilibration procedure will be lower, i.e., from about 2% to about 18% saturated.

Preferably, the interferon-alpha-2 is interferon alpha-2b and is more preferably human, recombinant crystalline interferon alpha 2b. In one embodiment, the crystalline material is interferon alpha-2b having the amino acid sequence shown below:

| Seq. I.D. No. 1 | | | | | | | | | | | | |
|---|---|---|---|---|---|---|---|---|---|---|---|---|
| 1 | Cys | Asp | Leu | Pro | Gln | Thr | His | Ser | Leu | Gly | Ser | Arg |
| 13 | Arg | Thr | Leu | Met | Leu | Leu | Ala | Gln | Met | Arg | Arg | Ile |
| 25 | Ser | Leu | Phe | Ser | Cys | Leu | Lys | Asp | Arg | His | Asp | Phe |
| 37 | Gly | Phe | Pro | Gln | Glu | Glu | Phe | Gly | Asn | Gln | Phe | Gln |
| 49 | Lys | Ala | Glu | Thr | Ile | Pro | Val | Leu | His | Glu | Met | Ile |
| 61 | Gln | Gln | Ile | Phe | Asn | Leu | Phe | Ser | Thr | Lys | Asp | Ser |
| 73 | Ser | Ala | Ala | Trp | Asp | Glu | Thr | Leu | Leu | Asp | Lys | Phe |
| 85 | Tyr | Thr | Glu | Leu | Tyr | Gln | Gln | Leu | Asn | Asp | Leu | Glu |
| 97 | Ala | Cys | Val | Ile | Gln | Gly | Val | Gly | Val | Thr | Glu | Thr |
| 109 | Pro | Leu | Met | Lys | Glu | Asp | Ser | Ile | Leu | Ala | Val | Arg |
| 121 | Lys | Tyr | Phe | Gln | Arg | Ile | Thr | Leu | Tyr | Leu | Lys | Glu |
| 133 | Lys | Lys | Tyr | Ser | Pro | Cys | Ala | Trp | Glu | Val | Val | Arg |
| 145 | Ala | Glu | Ile | Met | Arg | Ser | Phe | Ser | Leu | Ser | Thr | Asn |
| 157 | Leu | Gln | Glu | Ser | Leu | Arg | Ser | Lys | Glu | | | |

Interferon alpha-2a may also be employed. The primary amino acid sequence of interferon alpha-2a differs from the above sequence of interferon alpha-2b by the replacement of lysine for arginine at residue position 23.

The sulfate salt solution of interferon alpha-2 preferably includes a buffer having a pH of 6.5 to 8.5, more preferably from 7.3 to 8.0, such as a sodium phosphate buffer solution.

The crystalline interferon alpha-2 prepared by the above methods may be used as seed crystals for preparing additional crystalline interferon alpha-2.

DETAILED DESCRIPTION OF THE INVENTION

As noted above, the method of the invention involves equilibrating a sulfate salt solution of interferon alpha-2 against a sulfate salt solution that will cause the crystalline interferon alpha-2 solution to become more concentrated and form interferon alpha-2 crystals. Any suitable interferon alpha-2 can be employed, e.g., interferon alpha-2a and interferon alpha-2b, more preferably human, recombinant interferon alpha-2a (r-h-interferon alpha-2a) or interferon alpha-2b (r-h-interferon alpha-2b). Commercially available alpha-2 interferon preparations are available from Hoffmann-La Roche (Roferon®) and Schering-Plough (Intron®A). Mixtures of pure interferons including alpha-2 interferons are available from Burroughs-Wellcome Corporation (Wellferon®). In view of the high degree of sequence homology in the human interferonalphas, the method of the present invention should be applicable for each subspecies.

The human interferon alpha-2 subspecies may be obtained through recombinant DNA technology or may be pudfied from natural sources (e.g. human peripheral blood lymphocytes, human lymphoblastoid cell lines), for example, as described in Pestka, et al., *Ann. Rev. Biochem.*, 56, 727–777 (1987). A preferred interferon alpha-2 is r-h-interferon alpha-2b having the amino acid sequence as set forth above.

Natural human interferon alphas have been purified from several cell sources including leukocytes isolated from whole blood, neonatal fibroblasts, lymphoblastoid and various leukemic cell lines. The first clinically available preparation of human leukocyte interferon was developed by K. Cantell and associates in Finland, centrifuged blood from normal donors is pdmed with interferon, induced by addition of Sendal virus and centrifuged. The resulting supernatant is precipitated with potassium thiocyanate, extracted with ethanol, pH precipitated, and dialyzed against phosphate-buffered saline (K.E. Morgensen, L. Cantell (1977) Pharmacol. Ther. 1,369–381).

Recombinant interferon alphas have been cloned and expressed in *E. coil* by several groups, for example, C. Weissmann, et al. *Science* 209 (1980) 1343–1349. The purification of recombinant alpha-2 interferons has been described by several groups using a combination of chromatographic steps such as ammonium sulfate precipitation, dye affinity chromatography, ion exchange and gel filtration, for example, as described in Weissmann, C., *Phil R. Soc.* (Lond), (1982) b299, 7–28). An alternative approach for purifying recombinant interferon alphas employs immunoaffinity chromatography with an immobilized antibody (P.P. Trotta et al., *Developments in Iustrial Microbiology* 72, Elsevier, Amsterdam (1987) 53–64). For a review of available purification schemes used for recombinant alpha interferons, see T.L. Nagabhushan and P.P. Trotta, *Ullmann's Encyclopedia of Industrial Chemistry.* A14, VCH, Weinheim, Federal Republic of Germany (1989) 372–374. Preferably, the interferon alpha 2b used is purified by a conventional purification process described in *Ullmann's Encyclopedia of Industrial Chemistry.* A14, VCH, Weinheim, Federal Republic of Germany (1989) 372–374 followed by reversed phase high performance chromatography.

Suitable methods of equilibration include dialysis, ultrafiltration, e.g. diafiltration, or using drops, e.g., hanging or sandwiched droplets. Equilibration can be effected against a second sulfate salt solution that is more concentrated than the sulfate salt solution of interferon alpha-2. A particularly preferred method is to equilibrate a solution of r-h-interferon alpha-2 against a sulfate salt solution using a phosphate buffer solution. Preferably, the equilibration occurs slowly, e.g., over 2 to 30 days.

Large scale crystallization may be accomplished by methods equivalent to vapor diffusion: namely, dialysis and ultrafiltration. In clinical manufacturing, large scale crystallization can be used as a purification or concentration step. Furthermore, in such operation ammonium sulfate could be replaced by other common sulfate salts.

The final concentration of the interferon alpha-2 in the sulfate salt solution at the point of crystallization, i.e., at the point of first crystal formation, can range from about 10 to about 80 mg/mL. More preferably, the concentration of interferon alpha-2 is from about 30 to about 50 mg/mL. Preferably, the interferon alpha-2 starting concentration is about 20 rag/mi.

The concentration of the sulfate salt in the interferon alpha 2 solution at the initial stage prior to the start of crystallization procedures can range from about 2% to about 18% saturation, i.e., the sulfate salt present at 2 to 18% of the concentration which would be present if the solution were 100% saturated. More preferably, the concentration of the sulfate salt is from about 7% to about 15% saturated in the interferon alpha-2 solution. in the counter solution at the start of the crystallization procedure, the concentration of sulfate salt is from about 12% to about 30% saturation, more preferably, from about 15% to about 25% saturation.

The pH of the interferon alpha-2 solution and the counter sulfate salt solution is preferably controlled in the range of from about 6.5 to about 8.5, more preferably from about 7.3 to about 8.0. Any suitable buffer can be employed for this purpose. For example, sodium phosphate, Tris[hydroxymethyl]-aminomethane hydrochloride or N-[2, hydroxyethyl] piperazine-N'-[2-ethanesulfonic acid] buffers can be employed.

The crystallization preferably is performed under controlled temperature conditions. The temperature is preferably in the range of from about 15° to about 37° C., more preferably from about 18° to about 25 ° C.

Since the present invention surprisingly produces crystalline interferon alpha-2 at room temperature, it offers a distinct advantage over crystals obtained from polyethylene glycol at 4° C. Storage and formulation of human interferon-alpha 2 crystals at room temperature is now possible. Dissolution of the crystals can be accomplished by dialysis against 20mM sodium phosphate, pH 7.5 buffer with 0.15 M sodium chloride added. Moreover, since sulfate salt solution is easier to remove, e.g., by dialysis, than polyethylene glycol, purer interferon alpha-2 crystals can be obtained upon redissolution with the method of the invention.

The crystalline interferon alpha-2 prepared by the method of the invention will form the basis for various pharmaceutical formulations. For example, the crystalline interferon can be employed in a slow release formulation, e.g. a depot preparation capable of releasing the equivalent of a daily dose of 0.1–1.0 µg/kg body weight. A depot preparation employing crystals prepared by the method of the inventions should exhibit considerably slower rate of dissolution than a formulation containing crystals produced at 4° C. In particular, ambient temperature (22° C.) crystals should be less temperature sensitive than crystals that require a lower temperature of formation.

In addition, complexes of metals and human interferon alpha-2 can be formed then subsequently crystallized by the method of the invention. The crystals of such a complex could likewise be used in a slow release formulation. Examples of metal ion - protein complexes used in slow release formulation have been described in prior art. A complex of zinc and insulin prepared by the addition of zinc chloride to a sterile insulin solution was described in U.S. Pat. No. 2,882,203 assigned to Novo Terapeutisk Laboratorium A/S. The crystalline suspension of such complex was 4 to 6 times longer acting than a non-crystalline preparation (*Remington Pharmaceutical Sciences* 17, Gennaro, A.R., ed., Mack Publishing Co., Easton, Penna. (1985) 975–976). The zincinsulin complex is commercially available in different forms from several manufactures for example: Lente Insulin (Squibb), Ultra-Lente lietin (Lilly) and Ultralente Insulin/Ultratard (Squibb-Novo), *Remington Pharmaceutical Sciences* 17. Gennaro, A.R. ed., Mack Publishing Co., Easton, Penn. (1985) 975–976. Isophane Insulin is a crystalline product of insulin (zinc-insulin) and an alkaline protein (salmiddine). The product is manufactured under several trade names; NPH-Iletin (Lilly), Insulated (Leo) and Novolin N (Squibb-Novo) (Pharmaceutical Manufacturing Encyclopedia 1, Sittig. M. ed., (1988) 820–822). A zinc-interferon alpha-2 complex can be formed by methods described in U.S. Pat. No. 2,882,203. The interferon-alpha-2-zinc complex can be crystallized using the methods of this invention. The resulting crystalline suspension (comprising crystals of uniform size) formulated with appropriate additives (e.g. methylparaben, sodium chloride and sodium acetate) can be used for subcutaneous injection.

The crystalline interferon alpha-2 prepared by the method of the invention can be used in basically the same manner in which prior interferon alpha-2 materials have been used in pharmaceutical preparations, e.g., depot preparations of interferon alpha-2, which can be designed to administer a daily dose of about 0.1 µg/kg to about 1.0 µg/kg of crystalline interferon alpha-2. Such preparations contain a physiologically effective amount of the crystalline interferon alpha-2 in association with a conventional pharmaceutically acceptable carrier.

The invention disclosed herein is exemplified by the following working example, which should not be construed to limit its scope. Alternative methods within the scope of the invention will also be apparent to those skilled in the art.

The interferon alpha-2 employed was recombinant human interferon-alpha 2b expressed in *E. coil* as described in Weissmann, et al., *Science,* 209, 1343 (1980). The cells were cultured, harvested and extracted as previously reported in Leibowitz, P. et al (1982) U.S. Pat. No. 4,315,852. The resulting extracts was purified by a combination of conventional purification steps: ethanol extraction, matdx gel blue ligand affinity chromatography, ion exchange and gel filtration chromatography. The resulting purified interferon alpha-2b preparation was further purified by reversed-phase HPLC using a Rainin Auto Prep Chromatography system. Purified interferon alpha-2b (50mg) was chromatographed on a Rainin (4.1×250cm) $C_4$ 300 Angstrom column which had been pre-equilibrated with 27% acetonitrile, 0.1% trifluoroacetic acid (TFA). A linear gradient of 27%–72% acetonitrile, 0.1% TFA over a 30 minute pedod at 40ml/min was used to elute the interferon alpha-2b from the column. Eluted fractions were collected based on the absorbance profile from an in-line Knauer UV detector set at 280 nanometers.

Crystallization was achieved by vapor diffusion using either the hanging, sitting or sandwiched drop technique. Hanging drop vapor diffusion experiments were performed in 24 well tissue culture plates (Becton Dickinson and Company, Lincoln park, N.J.). Sandwiched drop experiments were performed in protein crystallization plates CrystaiPlate™ (Flow Laboratories, McLean, Va.) and sitting drop vapor diffusion experiments were performed in MVD/24 multi-chamber vapor diffusion plates (Cryschem, Inc., Riverside, Calif.).

For hanging droplets, 10 µl droplets containing 20 mg/mL of protein in 10% aqueous saturated ammonium sulfate, 40 mM sodium phosphate, pH 8.0 were hung from siliconized coverslips inverted on Linbro tissue culture plates. These droplets were equilibrated against 1 mL of 20% saturated ammonium sulfate, 40 mM sodium phosphate, pH 8.0. Large monoclinic prismatic crystals (0.5×0.5×0.5 ram) were evident anywhere from 4–15days of incubation at 22° C. Comparable solutions and experimental conditions were used for the sitting and sandwiched droplet experiments. The crystals were stable to X-ray diffraction analysis and diffracted to 6 A resolution. Different batches of crystals were subject to X-ray analysis and gave consistent results with respect to morphology. This is the first report of an X-ray diffraction pattern for interferon alpha-2.

For X-ray studies, crystals are mounted in glass capillaries and are photographed with a precession camera at 22° C. using CuKα radiation from a Rigaku RU-300 rotating anode generator operating at 40 kV and 100 mA. The native data set is collected on a Nicolet X-100A area detector using the same radiation source.

CHARACTERIZATION

1. BIOASSAY

Individual crystals were extracted from a hanging droplets with a syringe, then resuspended in 100 µl of wash solution consisting of 35% saturated ammonium sulfate, 40 mM sodium phosphate, pH 8.0 at 22° C. The suspension was centrifuged and the wash solution was removed with a Pasteur pipette. The washed crystals were redissolved in 100 µl of 20 mM sodium phosphate, pH 7.5, 0.15 M sodium chloride, at 22 ° C.

Protein was determined by a modified Bradford assay using pure human interferon alpha-2b as a reference standard. Antiviral activity was determined by a cytopathic inhibition assay using human foreskin diploid fibroblasts and encephalomyocarditis virus (ATCC-VR 129). A detailed description of the assay is provided in S. Rubinstein, P.C. Familletti and S. Pestka, J. Virol. 37 (1981) 755–758. The redissolved solution yielded a specific activity of $2.0 \times 10^8$ µlu/mg. This value is the same as that predicted for the original interferon alpha-2b preparation prior to crystallization, within the limits of the assay ( typically within the range $1 \times 10^8$ to $3 \times 10^8$ lu/mg).

2. HPLC

Analytical high performance liquid chromatography (HPLC) (Waters Ass. Milford, Mass.) was performed on an aliquot of redissolved interferon crystals. The sample was applied to a Rainin Dynamax $C_4$ 300 Angstrom column (4.6×250mm) which was subsequently eluted with a linear gradient of acetonitrile 27–72% in 0.1% trifluoroacetic acid over a 30 minute period. A Gilson variable wavelength detector set at 280nm with a sensitivity of 0.02 absorbance units was used to monitor the eluate. The retention times and chromatographic profiles of both the redissolved crystal solution and the original interferon alpha-2b preparation prior to crystallization were identical.

3. SDS-PAGE ANALYSIS

A comparison was made of interferon alpha-2b before and after crystallization by the one-dimensional 15% sodium dodecyl sulfate polyacrylamide gel electrophoresis (SDS-PAGE) method described in Laemmli, U. K. (1970) Nature 227, 680. There was no variation in relative mobility when the samples were compared in parallel lanes on the same gel.

From 1, 2 and 3 above, there is clearly no reason to suppose that any chemical changes or any denaturing of the protein took place during the crystallization or reconstitution.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method for the preparation of crystalline interferon alpha-2 which comprises equilibrating a first ammonium sulfate salt solution containing interferon alpha-2 against a counter ammonium sulfate solution under conditions that will cause the interferon alpha-2 solution to become more concentrated and form interferon alpha-2 crystals, wherein the ammonium sulfate is initially present in the first solution at a concentration of 10%, the interferon alpha-2 is present in the first solution at a concentration of from 10 to about 80 mg/ml at a point of first crystal formation, wherein ammonium sulfate is present in the counter solution initially at a concentration of 20% of saturation, and wherein the first solution and counter solution each have a pH of about 8.0.

2. The method of claim 1 characterized by the equilibration being effected by means of ultrafiltration or dialysis, or by vapor diffusion.

3. The method of claim 1, characterized by the equilibration being effected by vapor diffusion using hanging or sandwich droplets.

4. The method of claim 1, wherein the interferon alpha-2 is human, recombinant interferon alpha-2b.

5. The method of claim 1, wherein the ammonium sulfate salt solution containing interferon alpha-2 includes a buffer.

6. The method of claim 5 characterized by the buffer being sodium phosphate.

7. A method for the preparation of crystalline interferon alpha-2 which comprises equilibrating a first ammonium sulfate salt solution containing interferon alpha-2 against a counter ammonium sulfate salt solution under conditions that will cause the interferon alpha-2 crystals, wherein the ammonium sulfate is initially present in the first solution at a concentration of 10% of saturation, the interferon alpha-2 is present in the first solution at a concentration of about 20 mg/ml at a point of first crystal formation, wherein ammonium sulfate is present in the counter solution initially at a concentration of 20% of saturation, and wherein the first solution and counter solution each have a pH of about 8.0.

8. The method of claim 7 wherein the first and counter solutions each contain 40 mM sodium phosphate.

* * * * *